United States Patent
Rochat

(10) Patent No.: US 7,981,083 B2
(45) Date of Patent: Jul. 19, 2011

(54) PERFUSION OR ENTERAL/PARENTERAL FEEDING PUMP

(76) Inventor: Jean-Denis Rochat, Genolier (CH)

( * ) Notice: Subject to any disclaimer, the term of this patent is extended or adjusted under 35 U.S.C. 154(b) by 140 days.

(21) Appl. No.: 12/530,404

(22) PCT Filed: Mar. 5, 2008

(86) PCT No.: PCT/CH2008/000090
§ 371 (c)(1), (2), (4) Date: Sep. 8, 2009

(87) PCT Pub. No.: WO2008/106817
PCT Pub. Date: Sep. 12, 2008

(65) Prior Publication Data
US 2010/0114030 A1  May 6, 2010

(30) Foreign Application Priority Data
Mar. 8, 2007 (EP) ........................ 07405078

(51) Int. Cl.
*A61M 1/00* (2006.01)
(52) U.S. Cl. .................. 604/151; 417/417; 604/156
(58) Field of Classification Search .............. 417/299, 417/307, 415–417; 604/151, 153, 156
See application file for complete search history.

(56) References Cited

U.S. PATENT DOCUMENTS

| | | |
|---|---|---|
| 5,246,147 A | 9/1993 | Gross |
| 6,589,229 B1 * | 7/2003 | Connelly et al. ........... 604/890.1 |
| 2004/0127852 A1 | 7/2004 | Gray et al. |
| 2004/0220553 A1 * | 11/2004 | Olsen ........................ 604/891.1 |
| 2005/0191194 A1 * | 9/2005 | Falk et al. .................... 417/472 |
| 2010/0130934 A1 * | 5/2010 | Rochat ........................ 604/153 |

FOREIGN PATENT DOCUMENTS

| | | |
|---|---|---|
| WO | 93/23096 A1 | 11/1993 |
| WO | 2004/060435 A2 | 7/2004 |

OTHER PUBLICATIONS

International Search Report for PCT/CH2008/000090, mailing date of Jun. 2, 2008.

* cited by examiner

*Primary Examiner* — Nicholas D Lucchesi
*Assistant Examiner* — Gerald Landry, II
(74) *Attorney, Agent, or Firm* — Westerman, Hattori, Daniels & Adrian, LLP

(57) ABSTRACT

This pump with a battery-powered drive device comprises a circular elastic diaphragm (1a) and two valves (2b, 10), which has a diameter of 3 to 25 mm and is subjected to a compressive prestress of between $1'10^4$ and $4'10^4$ Pa capable of enabling it to return to its rest position at a maximum working frequency of between 8 and 12 Hz with a travel of between 0.2 and 2 mm, corresponding to a maximum flow rate of 1.5 to 2.5 l/h. The drive device comprises an electromagnet (5) in direct contact with the diaphragm (1a), a standard power supply battery, the available energy of which is from 7000 to 10'000 J, means for analyzing the supply current for the electromagnet and for detecting, at each pumping drive cycle, a minimum defined intensity of the supply current corresponding to the closure of the gap of the electromagnet (5) and means for interrupting the supply current once this minimum intensity has been reached.

8 Claims, 4 Drawing Sheets

PERFUSION OR ENTERAL/PARENTERAL FEEDING PUMP

This invention relates to an enteral, parenteral or infusion feeding pump with a battery-powered drive mechanism.

The pumps currently found on the market for this type of use are only able to run for a very short time. In most cases they are peristaltic pumps whose overall efficiency is very low, usually not exceeding 2%, sometimes well below 1%. When such a pump is powered by a battery of around 26 000 J and works against a pressure of around $2\times10^4$ Pa, it can only pump about 3 liters, which corresponds to 1.5 to 3 hours of operation depending on the flow rate. Recharging the battery from a mains adapter takes time and means that much of the time the pump is in use it is connected electrically to a wall socket. This is a serious brake on the spread of the use of pumps to replace drip and gravity infusion.

Peristaltic pumps have the intrinsic disadvantage of wasting a lot of energy due to friction severely reducing the amount of energy that can be used for the controlled delivery of the infusion liquid. Membrane pumps that have been used have large diameters and long strokes, and therefore cannot be used with a motor without mechanical speed reduction, which is itself a substantial source of loss of energy.

The object of the present invention is to substantially increase the amount of pumping that enteral, parenteral or infusion feeding pumps can pump on one battery charge by very significantly increasing the pump's efficiency, while ensuring optimal safety and a high degree of precision.

To this end, the present invention relates to an enteral, parenteral or infusion feeding pump as claimed in claim 1.

Not only is such a pump able to pump several tens of times more on one battery charge, but simultaneously it reduces the amount of energy required for its operation, making it possible to run the driving electromagnet on standard commercially available rechargeable 1.2 V AA or LR6 batteries, depending on the standard used. This greatly simplifies and reduces the work and cost of maintenance of these pumps, since these standard batteries are readily available on the market, notably in supermarkets, and at low cost.

Furthermore, the small size both of these pumps and of their drive mechanism makes them easy to use and install. The pump's small size and low energy requirements make it ideal for ambulatory use.

The accompanying drawing illustrates, schematically and by way of example, one embodiment of the pump of the present invention.

FIG. 1 shows a pump, especially a single-use pump, used in the medical field.

Figure 1:
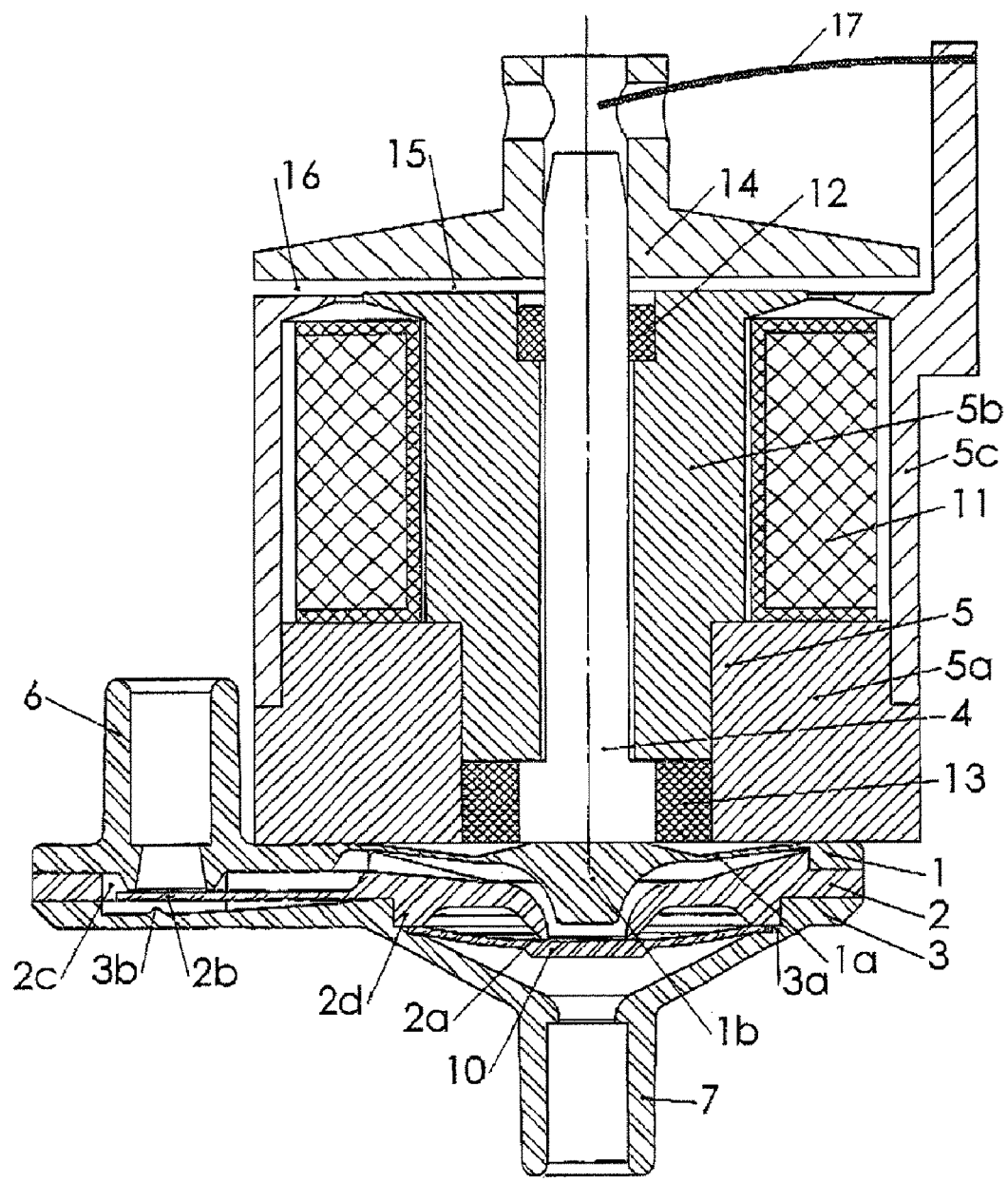
FIG. 1 shows this embodiment in elevation in cross section.

As can be seen, this single-use pump is essentially formed by an enclosure made up of three parts 1, 2, 3, two parts 1, 3 forming the wall of the pumping enclosure and one intermediate part 2. The wall parts 1, 3 comprise an intake duct 6 and a delivery duct 7, respectively. Wall part 1 has a thin part forming an annular membrane 1a surrounding a thick actuating part 1b. The thin annular part 1a acts as a pumping membrane while the thick central actuating part 1b transmits to the annular membrane the force applied by a pusher in the form of the moving core 4 of an electromagnet 5 which drives the pump. The deformation of the membrane 1a must of course remain within the limits of elastic deformability of the plastic of which wall part 1 is made.

The intermediate part 2 comprises a communication opening 2a for allowing selective communication between the upstream and downstream compartments of the pump. This communication opening 2a is in front of the thick central part 1b of the membrane and a valve 2b is situated in front of an opening 2c facing the inward end of the admission duct 6 formed in wall part 1. The opening 2a is at the end of a depression, while the thick central actuating part 1b forms a projection that engages in the opening 2a. The intermediate part 2 also comprises an annular projection 2b extending towards wall part 3, the role of which will be explained later.

Wall part 3 comprises a seat concentric with the delivery duct 7, for a valve 10 which controls the communication opening 2a of the intermediate part, which also acts as an anti-drip device, in order to prevent any liquid leaking out when the single-use is not inserted in the pump. This valve 10 is positioned between this communication opening 2a and the delivery duct 7 of the pump. To ensure that liquid cannot drip from the pump under gravity, the valve 10 is held against the opening 2a with a pressure of $4\times10^4$ Pa$\pm1\times10^4$ Pa.

In the rest position, it closes the opening 2a and is pressed against it as soon as the pressure difference between the upstream and downstream sides of the communication opening 2a is less than $4\times10^4$ Pa$\pm1\times10^4$ Pa. It moves away from this opening 2a as soon as the pressure difference mentioned above is greater than $4\times10^4$ Pa$\pm1\times10^4$ Pa.

Wall part 3 has an annular seat 3a for the valve 10. This valve 10 is retained on this seat 3a by the annular projection 2d of the intermediate part 2. Wall part 3 also has a projection 3b adjacent to the control valve 2b of the admission duct 6 to prevent this valve 2b pressing against the inside face of the wall 3. Given this arrangement, the face of the valve 2b not adjacent to the inward end of the admission duct 6 of the pump is exposed to the pressure of the compartment of the pump upstream of the communication opening 2a of the intermediate part 2. This valve 2b is thus able to close the inward end of the intake duct 6 when the pump is in its delivery phase and open it in the suction phase.

In order to give the pump described above a long battery life, a number of conditions must be met at the same time, both as regards the pump itself and its drive mechanism.

First of all, as regards the pump itself, the membrane 1a must have a relatively small diameter of between 3 and 25 mm, advantageously around 16 mm, in order to limit its actuating force, which is the product of the pressure P and the area S. Since the object is to move this membrane by means of an energy-saving electromagnet, it must also be small in size and the stroke of the membrane 1a, driven by the pusher core 4 of the electromagnet, is between 0.2 and 2 mm, advantageously around 0.5 mm. Under these conditions the stroke of the membrane 1a allows it to be driven directly by the piston core 4 of the electromagnet and avoids the need for mechanical speed reduction which would significantly reduce the overall efficiency of the pump.

The thickness of the elastic membrane 1a is advantageously between 0.1 and 0.7 mm, preferably around 0.3 mm. These dimensions allow the same thermoplastic to be used for both the membrane 1a and wall part 1 of the pump enclosure. This makes it possible to manufacture the part 1 and the membrane 1a in one and the same injection molding operation. Suitable thermoplastics include PC, PVC, ABS, PP and PE in particular. The choice depends on the cost, precision and stability of the elastic characteristics after sterilization and storage for a maximum period of three years. PC is the material which best meets this specification.

The electromagnet 5 that forms the reusable driving part of the pump is a cylindrical-pot electromagnet running on 5 volts. It therefore requires a voltage booster between the 1.2 V battery and the 5 V supply of the electromagnet. Its magnetic circuit comprises two air gaps, an inner air gap 15 and an outer air gap 16 either side of the coil 11 housing. In order to keep friction as low as possible, the piston core 4, made of hard metal, forming the moving part of the electromagnet 5 is guided in two lubricating ceramic bearings 12, 13. The piston core 4 is connected to the moving armature 14 of the electromagnet which has practically constant area of reluctance Sp. As can be seen in FIG. 1, in order to reduce the reluctances of the air gaps 15, 16 and maximize the force which they generate, both of them almost completely cover the coil 11 housing, and as a result the cylindrical pot of the electromagnet 5 must be made in three parts 5a, 5b, 5c.

The pot of the electromagnet 5 has a diameter of between 20 and 40 mm, typically 24 mm, and a height of between 15 and 25 mm, typically 20 mm. The fill factor of the housing of the electromagnet 5 pot by the coil 11 is around 80%. This coil 11 has an outside diameter of 18 to 24 mm, typically 21 mm, and a height of 9 to 14 mm, typically 11 mm. The area of reluctance Sp of the moving armature 14 is between 50 and 120 mm$^2$, typically 70 mm$^2$. The inner air gap 15 and outer air gap 16 are between 0.2 and 2 mm, preferably about 0.5 mm. In a preferred embodiment the inner air gap 15 is 0.5 mm and the outer air gap 0.6 mm.

Achieving a response time of the electromagnet suitable for the transfer times of the pumped liquid (typically 35 ms) giving maximum efficiency requires impedance matching between the source and the load.

To conserve power, the membrane 1a is designed to return by itself sufficiently rapidly to its rest position. To this end, this membrane 1a must be subjected, in the rest position, to a pressure preload of between $1\times10^4$ and $4\times10^4$ Pa, typically $2\times10^4$ Pa.

Figure 2:
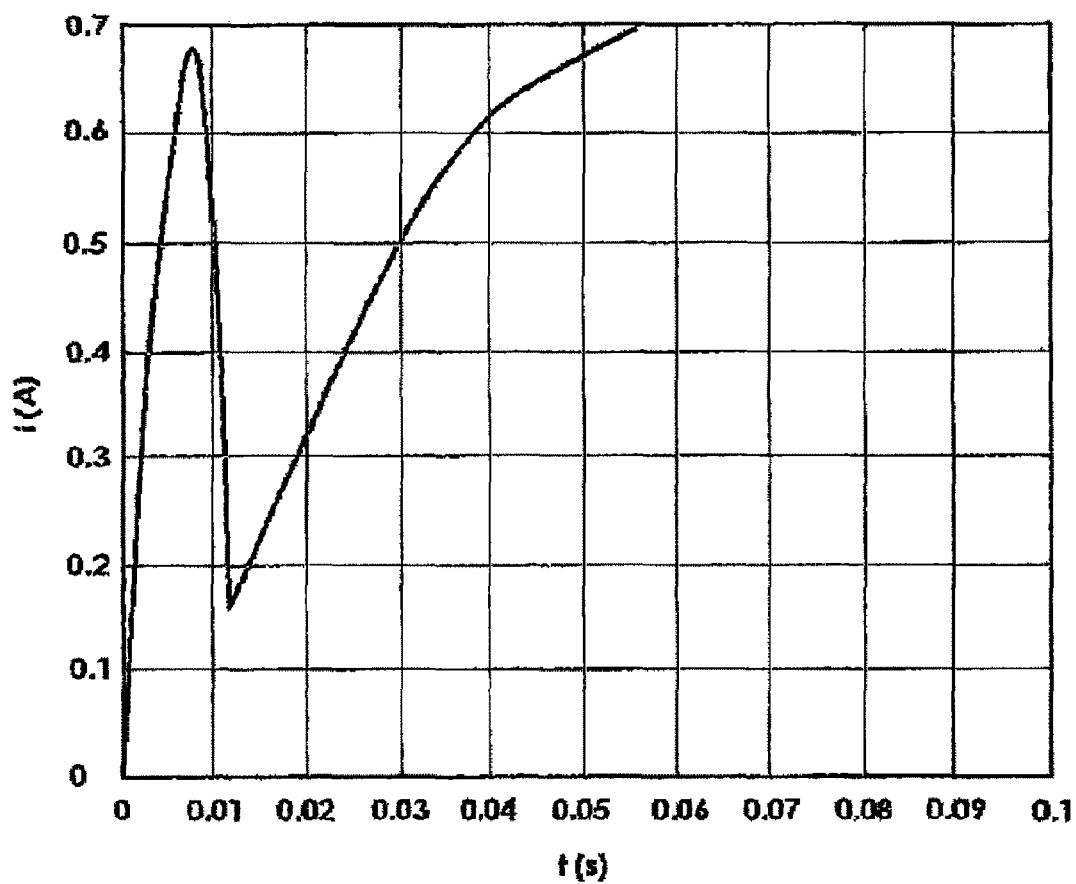
FIG. 2 is a diagram showing the curve of the current supplied to the electromagnet.

Since the only job of the electromagnet is to push the membrane 1a, the latter returning of its own accord to its rest position, the drive mechanism comprises means for analyzing the curve of the current supplied to the coil 11. This curve is illustrated in FIG. 2 and shows that the current passes first through a maximum and then through a minimum, corresponding to the air gaps 15, 16 closing. The current then rises again to reach the value $I=U/R$ where R is the resistance of the coil 11.

Figure 4:
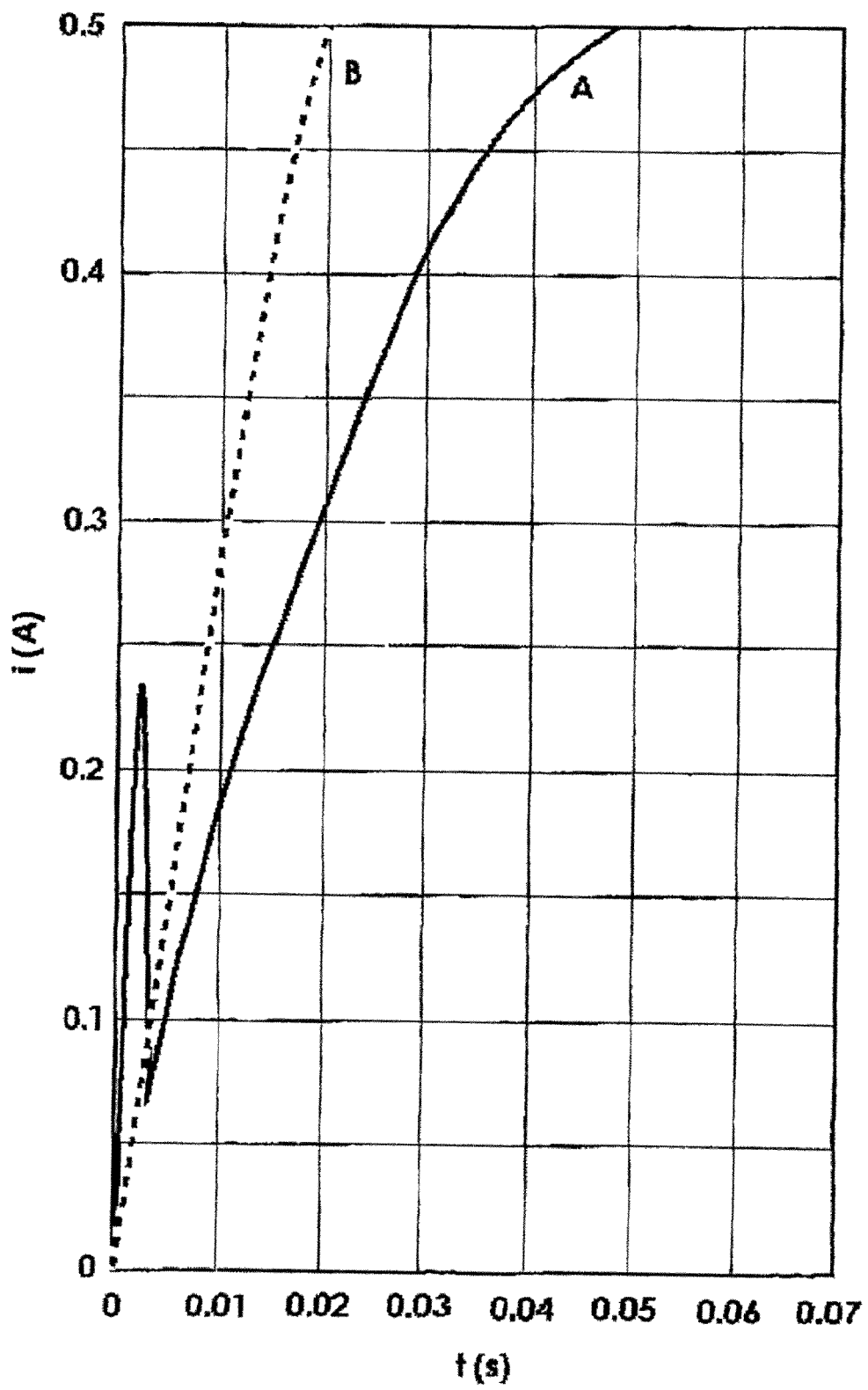
FIG. 4 is a diagram showing the curves of the current in the event of blockage upstream and downstream.

To conserve energy, the power supply system of the electromagnet 5 comprises means for analyzing the curve shown in FIG. 2 in order to detect the moment at which the curve of the current I passes through a minimum and to then interrupt, in every pumping cycle, the power supply to the electromagnet 5. The same analysis can be used to detect a blockage upstream of the duct, which is distinguished by the fact that the membrane fails to return to its rest position and the piston is then lifted back up by a very weak spring 17 which is only used to lift the piston (the spring 17 must overcome the forces of friction from the bearings and the weight of the piston, which comes to a total force of about 0.08 N), or downstream of the duct, as illustrated by curves A and B, respectively in FIG. 4, and thus to trigger an alarm.

Figure 3:
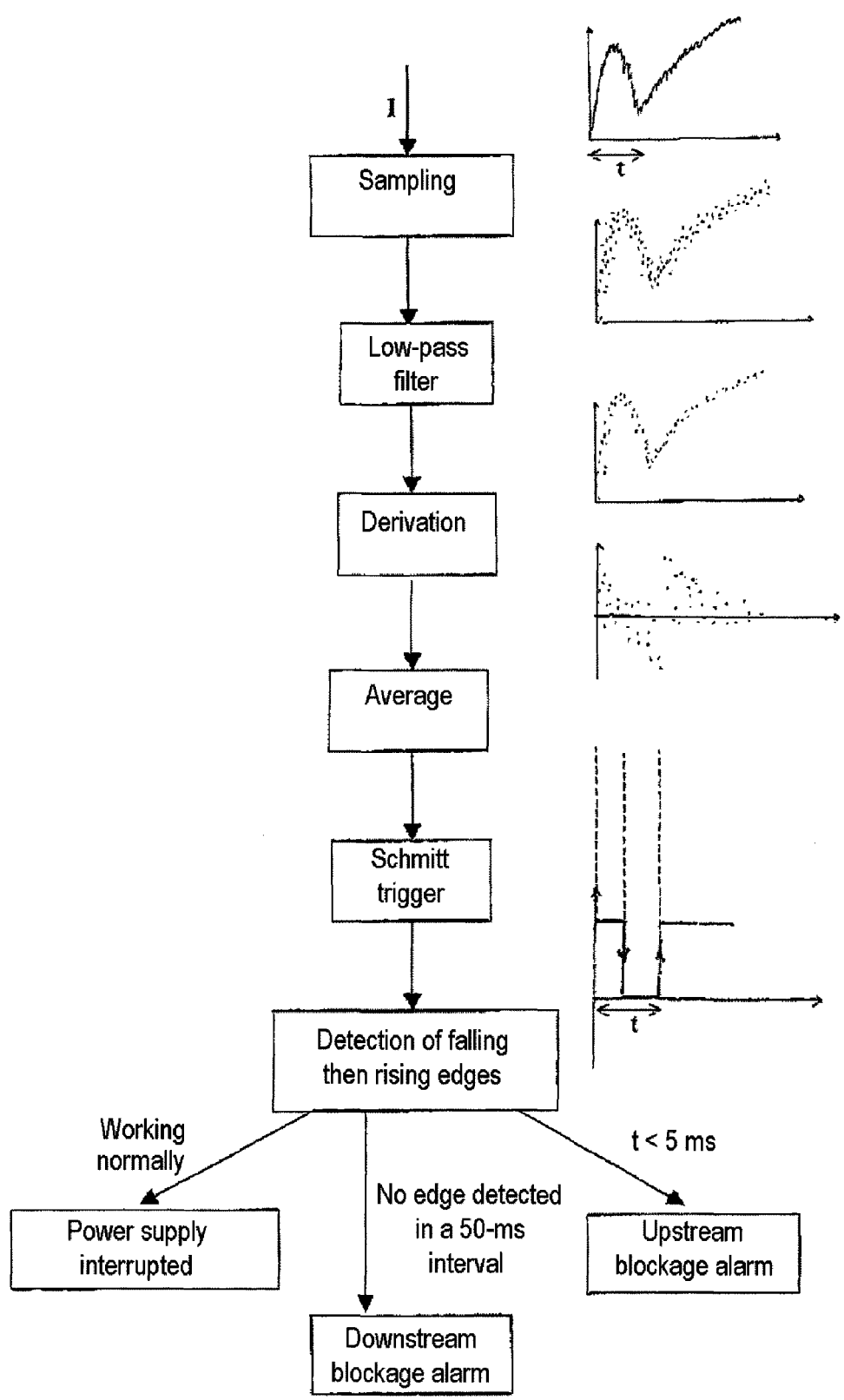
FIG. 3 is a diagram illustrating digital processing of the curve illustrated in FIG. 2.

In the example shown in FIG. 3, the signal is processed digitally but could also be processed by analog means.

The diagram in FIG. 3 illustrates the various steps in processing the signal with the changes to the signal as it is processed at each step. As will be seen, by the end of the process the system has detected the presence or absence of falling then rising edges at the end of the normal duration t of travel of the membrane 1a corresponding to the half-period of the pumping cycle. If these edges are detected, the pump is working properly and the power supply is interrupted until the end of the pumping cycle, as described earlier. This detection mode thus ensures that the electromagnet has reached the end of its travel, and thus that each volume pumped is precise.

In this example, assuming that the pump is running at a maximum frequency of 10 Hz, if at the end of 50 ms no edge has been detected, this means that the membrane 1a could not be moved because of a downstream blockage (curve B in FIG. 4) and the detection device triggers the downstream blockage alarm. If the detection device detects a falling edge in an interval t<0.5 ms, this means that there is an upstream blockage (curve A in FIG. 4) and the detection device triggers the upstream blockage alarm.

In the example described above, the volume pumped in each pumping cycle is 0.058 mL and the maximum pumping frequency is between 8 and 12 Hz, typically 10 Hz. This corresponds to maximum flow rates of between 1.5 and 2.5 L/h, typically 2 liters with an accuracy of around 5%.

With a rechargeable battery holding 7000 to 10 000 J, typically 8600 J, against a pressure of $2\times10^4$ Pa, the pump of the present invention can deliver 10 to 120 liters, typically 100 liters, on one battery charge. Under the same conditions a peristaltic pump with a rechargeable battery holding 26 000 J can pump 3 liters on one battery charge. This shows the enormous advance achieved by the present invention in the field of enteral, parenteral and infusion feeding pumps.

A comparison of the efficiencies of peristaltic pumps used for feeding, particularly with the pump of the present invention, has shown that the efficiencies are multiplied by a factor of practically 100 in the case of the present invention.

The invention claimed is:

1. An enteral, parenteral or infusion feeding pump with a battery-powered drive mechanism, comprising an elastic circular membrane and two valves situated upstream and downstream, respectively, of this membrane, which latter has a diameter of 3 to 25 mm and is subjected to a pressure preload of between $1\times10^4$ and $4\times10^4$ Pa such as to enable it to return to its rest position at a maximum working frequency of between 8 and 12 Hz with a stroke of between 0.2 and 2 mm, corresponding to a maximum flow rate of 1.5 to 2.5 L/h and the drive mechanism comprises an electromagnet whose moving part is directly connected to said membrane, a standard battery to power this electromagnet with an available energy of 7000 to 10 000 J, means for analyzing the electromagnet supply current and detecting in each pump drive cycle a predetermined minimum value of the supply current corresponding to closure of the air gap of the electromagnet, and means for interrupting the supply current once this minimum value is reached, in order to ensure that one battery charge cycle can pump between 10 and 120 liters.

2. The pump as claimed in claim 1, in which the circular membrane has a diameter of between 12 and 20 mm, the pressure preload is around $2\times10^4$ Pa, the maximum working frequency is around 10 Hz, the stroke of the membrane is between 0.4 and 0.8 mm, the maximum flow rate is 2 L/h, and the energy of the battery powering the electromagnet is from 8000 to 9000 J, allowing one battery charge cycle to pump from 80 to 100 liters.

3. The pump as claimed in claim 1, in which the valve situated downstream of the membrane is pressed against its seat in the rest position with a pressure of $4\times10^4$ Pa$\pm1\times10^4$ Pa.

4. The pump as claimed in claim 1, comprising means for analyzing the variation of the electromagnet supply current and detecting a variation characteristic of a blockage upstream or downstream of the pump, these means for analyzing the variation of the current being connected to an alarm device to activate it when they detect that the curve of the supply current is characteristic of a blockage upstream or downstream of the pump.

5. The pump as claimed in claim 1, in which the electromagnet operates at a voltage of 5 V an has a cylindrical pot with two air gaps, an inner air gap and an outer air gap <1 mm, partially covering the coil whose diameter is from 20 to 40 mm and whose height is from 12 to 20 mm, with a fill factor of around 80%, and whose moving part has an approximately constant area of reluctance Sp.

6. The pump as claimed in claim 1, in which the power supply battery is a 1.2 V rechargeable battery holding 8600 J or more.

7. The pump as claimed in claim 1, in which the piston core, made of hard metal, of the electromagnet is guided in two self-lubricating ceramic bearings.

8. The pump as claimed in claim 4, in which the moving part of the electromagnet is provided with a spring whose force is calculated to overcome the forces of friction and of weight of the moving part of the electromagnet in order to return this moving part to the rest position in the event of an upstream blockage.

* * * * *